United States Patent [19]

Van Steenburg

[11] Patent Number: 4,898,491

[45] Date of Patent: Feb. 6, 1990

[54] LOCKING PIVOT ASSEMBLY WITH BOTH PIVOT AND TILT AXES

[75] Inventor: Kip Van Steenburg, Sudbury, Mass.

[73] Assignee: Amatech Corporation, Acton, Mass.

[21] Appl. No.: 104,839

[22] Filed: Oct. 5, 1987

Related U.S. Application Data

[63] Continuation-in-part of Ser. No. 710,050, Mar. 11, 1985, Pat. No. 4,698,837.

[51] Int. Cl.$^4$ ............................................. F16C 11/04
[52] U.S. Cl. ...................................... 403/96; 403/97; 403/146
[58] Field of Search ...................... 403/97, 96, 92–94, 403/146

[56] References Cited

U.S. PATENT DOCUMENTS

| | | | |
|---|---|---|---|
| 2,410,560 | 11/1946 | Witte | 403/96 |
| 2,922,669 | 1/1960 | Hansen | 403/96 |
| 3,433,511 | 3/1969 | Frankel | 403/96 |
| 3,591,216 | 7/1971 | Onufer | 403/146 |
| 4,018,104 | 4/1977 | Bland et al. | 403/146 X |
| 4,614,452 | 9/1986 | Wang | 403/146 X |
| 4,731,896 | 3/1988 | de La Tour | 403/97 X |

*Primary Examiner*—Randolph A. Reese
*Assistant Examiner*—Peter M. Cuomo
*Attorney, Agent, or Firm*—Joseph S. Iandiorio

[57] ABSTRACT

A pivot assembly including a rotating member, a mounting member for supporting the rotating member, and a pivotal interconnection for the members. The interconnection enables rotation about a pivot axis and inhibits translation of the rotating member relative to the mounting member along the pivot axis. There are also structure enabling tilting of the rotating member about a tilt axis transverse to the pivot axis, and gripping elements for inhibiting relative rotation about the pivot axis. The gripping elements increase grip between the adjacent sections when the rotating member is tilted about the tilt axis in a first direction, and decrease grip when the rotating member is tilted about the tilt axis in a second and opposite direction to enable rotation of the rotating member.

20 Claims, 5 Drawing Sheets

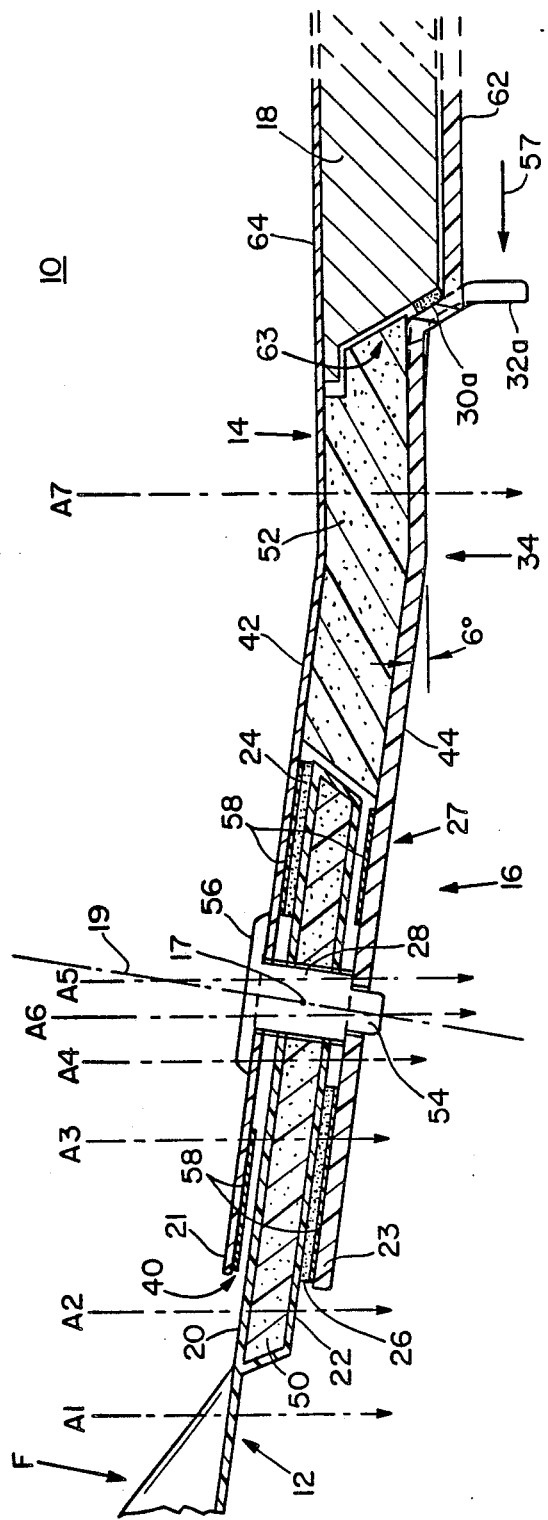

LOCKING PIVOT ASSEMBLY WITH BOTH PIVOT AND TILT AXES

RELATED APPLICATION

This application is a continuation-in-part of U.S. Ser. No. 710,050 filed Mar. 11, 1985 to be issued on Oct. 6, 1987 as U.S. Pat. No. 4,698,837.

FIELD OF INVENTION

This invention relates to a locking pivot assembly for a rotating member such as an armboard, and more particularly to a pivot assembly having a locking system which disengages when rotated about a tilt axis to enable rotation of the armboard about a pivot axis.

BACKGROUND OF INVENTION

There are a number of positionable devices which are rotated to a desired orientation. One such device is an armboard which is rotatably associated with an X-ray table.

Cardiac, neurological and general vascular studies frequently require an X-ray table for examining patients. Viewing a patient's body is particularly important for guiding catheters through arteries or veins. The body is frequently accessed through an arm of the patient positioned on an armboard of an armboard mounting assembly. This technique is commonly referred to as the Sones approach. An armboard mounting assembly has an armboard mount attached to the X-ray table for mounting one or more armboards which extend from the mounting assembly at a pivot assembly.

An X-ray table typically rests between a radiological source, such as an X-ray tube, and an imaging plate responsive to a viewing screen or including an imaging film. Most areas of conventional tables and armboards are by necessity radiologically translucent to allow X-rays to reach the imaging plate. However, important areas of X-ray tables and accessories often contain radiologically opaque structural material such as steel. Details of the patient's body overlaying the opaque structure are obscured and physicians must navigate a catheter blindly through these bodily regions. One such region is the patient's shoulder overlaying the pivot assembly between the armboard and the armboard mount. A conventional armboard has a steel pin protruding from a steel disk embedded in the board. Steel is used to provide strength and durability. Radiological opacity of the conventional pivot assembly presents great difficulty in passing a catheter through the proper vein or artery in the shoulder area. Further, the pivot assembly is often attached to the armboard mount with steel connector pins. Commonly, the connector pins insert into a steel cradle mount which bridges the X-ray table and provides support for opposing armboards. These radiologically opaque structures further reduce the effective viewing areas of a patient.

Conventional armboards exhibit other disadvantages. Accepted hospital practices prevent radiologists from touching objects outside the sterile zone. The locking mechanism for many armboards are located on the underside of the armboard and table in a non-sterile area, where it may not be accessed during medical procedures. Thus the need to move the armboard and the restriction against touching non-sterile areas can create a conflict for the attending physicians. These locks are active locking systems requiring action to lock or unlock them. When locked, it is possible to damage them through forcible, inadvertent movement. Armboard mounts are secured with separate active locking systems often involving screw or clamps which are not X-ray translucent.

The metal components associated with conventional armboard designs make them incompatible with NMR procedures. NMR scanning requires that the study area be free of ferrous or other magnetic material which is or can become magnetized. The magnetic material interferes with the varying magnetic field used in NMR procedures. The study area must also be free of electrically conductive material for the safety of the patient and the attendants. These requirements have prevented the use of a pivoting, locking armboard during such procedures.

One conventional armboard mount is not radiologically translucent and relies on an upward translational movement of the armboard to disengage the armboard and enable rotation to a desired position. However, the weight of the entire arm of the patient must be overcome to accomplish the translational disengagement.

SUMMARY OF INVENTION

It is therefore an object of this invention to provide an improved pivot assembly having an improved locking system for selectively locking a rotating member relative to a mounting member.

It is a further object of this invention to provide such a locking system which is passive and self-locking.

It is a further object of this invention to provide for an armboard mounting assembly an improved locking system which is locked by the weight of a patient's arm.

It is a further object of this invention to provide such a locking system which reduces the possibility of damage to the armboard from forcible movement.

It is a further object of this invention to provide such a locking system which is simply constructed and easy to repair and maintain.

It is a further object of this invention to provide such a locking system which provides easy operation without violating the sterile zone.

It is a further object of this invention to provide such a locking system for use in NMR procedures that is free of all magnetic and electrically conductive materials.

Yet another object of this invention is to provide an improved pivot assembly which is radiologically translucent.

It is a further object of this invention to provide such a pivot assembly having a more uniform attention profile.

It is a further object of this invention to provide such a pivot assembly providing smoother, easier rotation of the armboard.

It is a further object of this invention to provide such a pivot assembly which is NMR-compatible.

This invention results from the realization that truly effective rotatable and lockable interconnection of a rotating member and a mounting member can be achieved by pivotably interconnecting the members to enable rotation about a pivot axis while inhibiting translation of the rotating member along the pivot axis, enabling tilting of the rotating member about a tilt axis transverse to the pivot axis, and providing one or more gripping elements which increase gripping when the rotating member is tilted about the tilt axis in one direction, thereby holding the rotating member at a desired orientation, and which decrease gripping when the rotating member is tilted about the tilt axis in the opposite direction to enable the rotating member to be reoriented.

This invention features a pivot assembly including a rotating member, a mounting member for supporting the rotating member, and means for pivotably interconnecting the rotating member and the mounting member to enable rotation about a pivot axis, and for inhibiting translation of the rotating member relative to the mounting member along the pivot axis. The rotating member and the mounting member overlap to define at least one pair of adjacent sections, and the pivot assembly further includes means for enabling tilting of the rotating member about the tilt axis transverse to the pivot axis, and means for providing gripping between the adjacent sections to inhibit relative rotation about the pivot axis. The means for gripping increases grip between the adjacent sections when the rotating member is tilted about the tilt axis in the first direction, and decreases grip when the rotating member is tilted about the tilt axis in a second and opposite direction.

In one embodiment, the means for enabling includes means for defining a space between the rotating member and the mounting member. The rotating member tilts into the space during tilting about the tilt axis in the second direction. The means for defining may include spring means for biasing the rotating member and the mounting member away from each other, or the means for defining may be a portion of one of the members. Alternatively, the means for enabling includes hinge means associated with the rotating member such as structure hingeably joining a segmented rotating member. The means for enabling may instead include flexible material forming at least a portion of the rotating member. The means for enabling may establish the tilt axis as spaced from and substantially normal to the pivot axis.

In another embodiment, the means for providing gripping includes a friction member mounted on at least one of the adjacent sections and providing frictional resistance to relative motion of the adjacent sections. Alternatively, the means for providing gripping includes a detent on one of the adjacent sections and at least one recess on another for receiving the detent. The mounting member may include a pair of spaced segments for receiving the proximate end of the rotating member therebetween, and the members define two pairs of adjacent sections and the means for providing gripping includes engaging means mounted on at least one of each of the pair of sections. The means for pivotably interconnecting may include a pivot pin which has a head which inhibits translation of the rotating member and means, spaced from the head, for engaging the mounting member. The members, the means for pivotably interconnecting, the means for enabling rotation, and the means for providing gripping may be radiologically translucent and consist of non-magnetic and electrically non-conductive materials. The rotating member may be an armboard and the mounting member may be an armboard mount.

DISCLOSURE OF PREFERRED EMBODIMENTS

Other objects, features and advantages will occur from the following description of a preferred embodiment and the accompanying drawings, in which:

FIG. 2 is a cross-sectional view along lines 2—2 of FIG. 1 showing the gripping elements and other features of the pivot assembly;

FIG. 3 is an axonometric view of an alternative gripper for use in the pivot assembly shown in FIG. 2;

Figure 1:
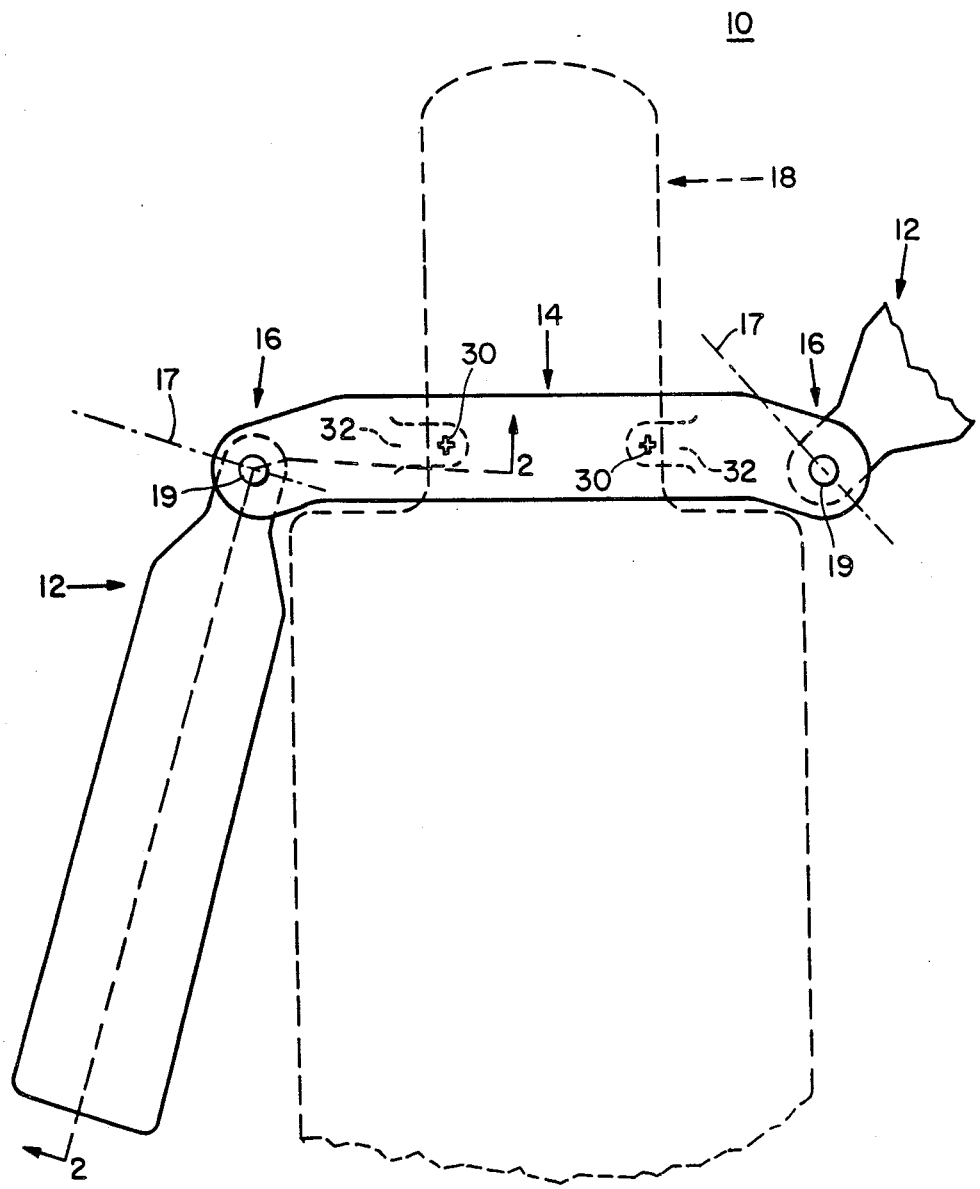
FIG. 1 is a plan view of an armboard mounting assembly mounted on an X-ray table and including an armboard, an armboard mount, and a pivot assembly according to the present invention having both pivot and tilt axes.

This invention may be accomplished by a pivot assembly having a rotating member, a mounting member for supporting the rotating member, and a pivot interconnection for enabling rotation of the rotating member about a pivot axis. The pivot interconnection also inhibits translation of the rotating member relative to the mounting member along the pivot axis. The pivot assembly further includes structure which enables tilting of the rotating member about a tilt axis transverse to the pivot axis, and gripping elements which increase gripping between the rotating member and the mounting member to inhibit relative rotation about the pivot axis when the rotating member is tilted about the tilt axis in a first direction, and decrease gripping when the rotating member is tilted about the tilt axis in a second and opposite direction.

In one construction, the rotating member is an armboard and the mounting member is an armboard mount. Armboard mounting assembly 10 is shown in FIG. 1 having armboards 12 and armboard mount 14 with integral pivot assemblies 16 according to this invention which together rotatably support the arms of a patient lying on X-ray table 18, shown in phantom.

Rotation of armboards 12 about pivot axis 19 is inhibited when armboards 12 are tilted downwardly about tilt axes 17. Conversely, tilting of armboards 12 in the opposite direction of about tilt axes 17 releases armboards 12 and enables rotation about pivot axes 19. The locking system of pivot assemblies 16 is described in more detail below.

Radiologically translucent components of a pivot assembly according to this invention can be arranged to provide uniform radiological attenuation across a vertical profile of the armboard mounting assembly, facilitating examination of the patient. When the components are composed of non-magnetic and electrically non-conductive materials, the armboard mounting assembly can be used for NMR procedures.

Armboard mount 14, FIG. 1, secures armboard mounting assembly 10 to an object such as X-ray table 18. Preferably, armboard mount 14 includes two mount gripping means 30, disposed on biasing members 32, for engaging X-ray table 18 on which armboard mount 14 is installed.

Armboard mount 14 is angled upwards, FIG. 2, at region 34 at an angle of six degrees to provide a more comfortable position during rotation for a patient's arm located on armboard 12. Region 34 is located beneath the scapula of an average patient when lying on table 18. Armboard 12 rotates about pivot axis 19, corresponding to the longitudinal axis of pivot pin 28, when armboard 12 is tilted upwardly about tilt axis 17. The proximate end of armboard 12 includes circular insert 40 having edges slanted at approximately a forty-five degree angle as discussed below. Insert 40 rests between two skins of armboard mount 14, designated spaced segments 42, 44. Section 20 of insert 40 is adjacent to section 21 of segment 42, and section 22 of insert 40 is adjacent to section 23 of segment 44. Grippers 24, 26 of locking system 27 are mounted on the surface of sections 20, 22, respectively, and include a friction member composed of material such as natural gum rubber or Urethane Rubber, available from Parkway Rubber, Ohio.

Alternatively, these high-friction brake members may be recessed into sections 20, 22. As described below, the area and thickness of these members affect radiological attenuation profiles. In yet another arrangement, the brake member may be one or more annular friction rings mounted about the circumference of a non-rotating pivot pin, the pivot pin being affixed to segment 42, 44, or both.

A downward force having a vector in the direction indicated by arrow F brings grippers 24, 26 of locking system 27 against sections 21, 23 of spaced segments 42, 44, respectively, to increase gripping between these sections. The weight, however slight, of armboard 12 itself typically causes some engagement between grippers 24, 26 and sections 21, 23, respectively; alternatively, the initial engagement is negligible or nonexistent. Engagement is increased by additional downward force on armboard 12. The force such as that provided by the weight of a patient's arm is generally transverse to the direction of rotation and generally parallel to the pivot axis. Grippers 24, 26 oppose and restrict rotation but do not absolutely prevent rotation when normal downward force is applied to armboard 12.

Tilting of armboard 12 about tilt axis 17 is provided in this construction by a slight gap between insert 40 and pivot pin 28 which enables tilting motion. In other constructions tilting is further enabled by the flexing of pin 28. Translational movement of armboard 12 proximate pin 28 is inhibited by the lower portion of section 21 as well as by head 56 of pin 28.

While tilting axis 17 is described as an axis passing through pivot pin 28, axis 17 is actually the net axis of rotation of armboard 12 in a vertical plane. That is, during vertical movement of armboard 12, the actual tilting axis wanders. As shown in FIG. 2, when the distal end of armboard 12 is raised, insert 40 pivots first on the proximal edge of gripper 26, then the lower proximal edge of insert 40 pivots against section 23, and the upper, distal portion of insert 40 pivots against the distal edge of section 21. Net tilting motion, however, occurs generally about tilting axis 17 as indicated.

Locking system 27 in some constructions utilizes mechanical gripping instead of frictional gripping. Instead of friction members, locking system 27 may include a detent and recess arrangement to engage at least one pair of adjacent sections between armboard 12 and armboard mount 14. Gripper 24a, FIG. 3, includes detent portion 70 which has projection 72 to engage one of the recesses 74 of recess portion 76. Gripper 24a may be located in the same region as gripper 24, FIG. 2, such that detent portion 70 and recess portion 76 are mounted on sections 20 and 21, respectively, of pivot assembly 16. It is desirable that either detent portion 70 or recess portion 76, or both, be arcuate such that armboard 12 may be moved through a large angle until its rotation is inhibited by application of downward force to the armboard. A rosette segment of 160–180 degrees, for example, may serve as recess portion 76.

To provide more uniform attenuation across a vertical section of pivot assembly 16, FIG. 2, radiologically translucent materials are preferred for armboard mounting assembly 10 including pivot assembly 16 according to this invention when intended for radiological use. An acceptable material for radiological use of armboard 12 and armboard mount 14 is carbon fiber. Kevlar, available from Exxon Materials Division and n Uniroyal, is also suitable, although somewhat thicker cross-sections are required to provide strength similar to carbo fiber. Insert 40 of armboard 12 may contain a core 50 and armboard mount 14 may contain core 52, the cores composed of ABS plastic material, without fire retardant additives, available from Uniroyal, or a phenolic material such as Micarta. Pivot pin 28 includes shouldered post 54 and head 56 and may also be formed from ABS plastic or Micarta. Pin 28 may be held in place simply by a piece of adhesive tape and may be formed without head 56.

A smooth durable braking surface is provided by wear-resistant materials such as Mylar 58, FIG. 2, disposed about the braking surfaces of sections 21 and 23 of segments 42 and 44, respectively. Mylar is particularly effective when the friction member is rubber since these two materials exhibit a high coefficient of friction when forced against each other. Mylar also provides slight radiological attenuation and is used to balance the attenuation caused by other elements in pivot assembly 16. Depending on the attenuation characteristics of these other elements, Mylar or thin aluminum foil is disposed about at least one of the adjacent sections 20, 21, 22 and 23 to compensate for the attenuation provided by friction member grippers 24, 26 and to balance the attenuation of pivot pin 28.

Figure 4:
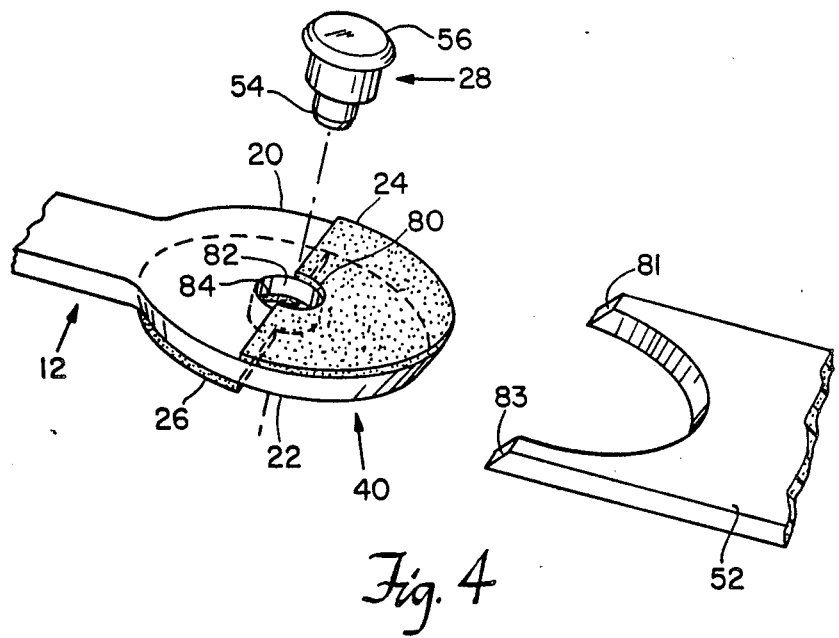
FIG. 4 is a partial axonometric view of the pivot assembly shown in FIG. 2.

Friction member grippers 24, 26 are semicircular in shape and mounted on sections 20, 22 as shown in FIG. 4. Grippers 24, 26 have openings 80 and 84, respectively, corresponding to the opening 82 in insert 40 for receiving pivot pin 28. The chamfered edge of post 54 projects through armboard mount segment 44 (not shown), while pin head 56 rests on the surface of segment 42 (not shown).

The end of core 52 that faces armboard insert 40 is semi-circular in shape to admit insert 40, FIG. 4. Core 52 projects outwardly on either side of insert 40 nearly as far as opening 82; the rotational boundaries of armboard 12 are determined by projections 82, 83. Core 52 is bonded to skin segments 42, 44 (not shown) to supplement tensile and compressive strengths of the two skins. Additional strength may be added by merging segment 44 with edges of segment 42 to enclosed the longitudinal sides of core 52.

The details of radiologically translucent components for one embodiment of the armboard mounting assembly, using the reference numerals of FIG. 2, are provided in Table I:

TABLE I
DETAILS OF ARMBOARD MOUNTING ASSEMBLY COMPONENTS

| REFERENCE NUMERAL | ELEMENT | MATERIAL | THICKNESS (inch) | ATTENUATIONS (in mm aluminum) |
|---|---|---|---|---|
| 24, 26 | Friction Members | Urethane | .060 | .152 |
| 28 | Pivot Pin without Head and Post | A.B.S. | .655 | 1.529 |
| 12 | Armboard | carbon fiber | .060 | .225 |
| 50 | Armboard Insert Core | A.B.S. | .190 | .443 |
| 58 | Mylar | Mylar | .005 | .012 |
| 42 | Armboard Mount Segment, Top | carbon fiber | .060 | .255 |
| 44 | Armboard Mount Segment, Bottom | carbon fiber | .100 | .425 |
| 52 | Armboard Mount Core | A.B.S. | .375 | .874 |
| 56 | Pin Head Only | A.B.S. | .070 | .163 |
| 54 | Pin Post Only | A.B.S. | .180 | .419 |

The attenuation values in mm aluminum equivalents are approximations since attenuation does not vary linearly with thickness; the values are extrapolated from studies of similar thicknesses. For these components, vertical attenuation characteristics at viewing slice points indicated by dashed lines A1 through A7 are summarized in Table II:

TABLE II
VERTICAL ATTENUATION CHARACTERISTICS OF ARMBOARD MOUNTING ASSEMBLY

| SLICE | ELEMENT NO. COMBINATION | ATTENUATION (in mm aluminum) |
|---|---|---|
| A1 | 12 | 0.26 |
| A2 | 12 + 50 | 0.70 |
| A3 | 42 + 58 + 12 + 50 + 26 + 58 + 44 | 1.56 |
| A4 | 56 + 42 + 58 + 12 + 50 + 44 | 1.54 |
| A5 | (28–54) + 44 | 1.53 |
| A6 | 28 | 1.53 |
| A7 | 42 + 44 + 52 | 1.55 |

For example, radiological viewing slice A1 passes through only highly transparent armboard 12 having an attenuation of 0.26 of aluminum. Radiological slice A3 passes through armboard mount segments 42, 44, armboard 12, armboard insert core 50, friction pad 26, and two layers of Mylar 58 disposed on sections 21, 23. The components seen in view A3 provide an attenuation equivalent to 1.56 mm of aluminum.

Thus, a difference of only 0.03 mm aluminum-equivalent attenuation is provided in this example between viewing slices A3–A7 including the crucial pivot assembly components. While the slice attenuation values in Table II are based on approximations of the attenuation values for each element, the relative differences among the slice attenuation values are fairly accurate as presented. The slanted edges of armboard insert 40 and armboard mount core 52, FIGS. 2 and 4, further reduce transitions in the attenuation profile. The density, thickness, and shape of these elements are varied after fluoroscopic observation until a minimum level of contrasts is provided across the attenuation profile. The materials appropriate for NMR use are discussed below.

Figure 5:
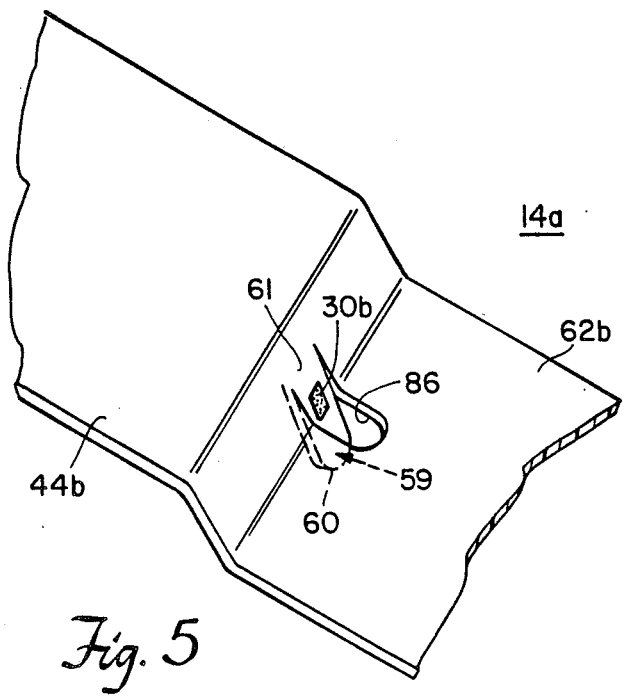
FIG. 5 is an axonometric view of a mount gripping means and biasing member.

In one embodiment, biasing member 32a, FIG. 2, is a flexible element formed of carbon fiber, and is 0.100 inch in thickness, approximately ⅝ of an inch in width, and approximately 1½ inches long. The two edges and terminal end 60 of flexible element 59, FIG. 5, are cut out of the materials of armboard mount 14a, including segment 44b and leg 62b, leaving end 61 attached and integral with the material. Friction member 30b is urged through opening 86 by flexible element 59 except when terminal end 60 of flexible element 59 is forced away from leg 62b by external pressure, bringing friction member 30b to the position shown in FIG. 5.

To adjust the position of armboard mounting assembly 10, outward pressure, arrow 57, FIG. 2, is applied to biasing member 32a near its terminal end to overcome its urging of friction member 30a against table 18. For example, a medical attendant may reposition armboard mounting assembly 10 by placing one thumb of each hand between flexible element 59 and table 18, applying force outwardly, arrow 57, from table 18 to both flexible elements 59 and moving armboard mount 14 toward or away from him.

Figure 6:
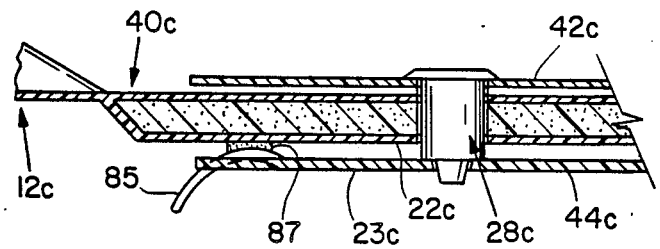
FIG. 6 is a partial cross-section view along lines 2—2 of FIG. 1 of an alternative pivot assembly according to this invention.

A similar arrangement of one of more biasing members and friction members can be used as the locking mechanism in a pivot assembly according to this invention. Member 85, FIG. 6, is located on section 23 of segment 44c and engages section 22c of armboard inset 40c. When biasing member 85 is a flexible element similar to flexible element 59, FIG. 5, its terminal end is also manually depressible to move the friction member away from adjoining section 22c of insert 40c to thereby allow rotation of armboard 12c about pivot pin 28c. Downward force on armboard 12c, although not necessary in this arrangement to inhibit rotation, will increase pressure and therefore friction between the friction member 87 and adjoining insert section 22c. Therefore, this arrangement is also responsive to downward force on armboard 12c to increase gripping between sections 22c and 23c.

When intended for NMR use, the armboard mounting assembly must not contain magnetic or electrically conductive materials. Urethane rubber, natural gum rubber, Mylar, A.B.S. plastic, and Kevlar are all compatible with NMR procedures. Another acceptable material is unidirectional, high-strength fiberglass. Unidirectional fiberglass or Kevlar may be used as the skins of armboard 12 and armboard mount 14 instead of carbon fiber. Since radiological attenuation is not considered in NMR procedures, the components are readily increase in thickness to provided increased structural strength.

Figure 7A:
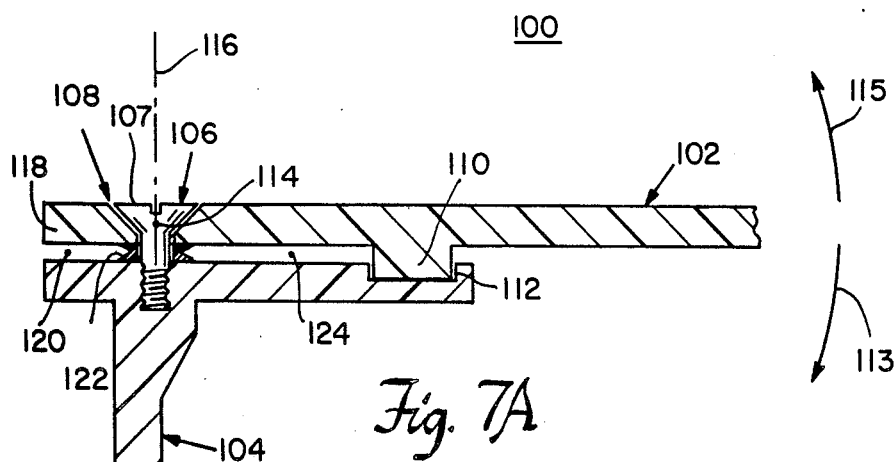
FIG. 7A is a schematic cross-sectional view of yet another pivot assembly according to this invention for selectively locking a rotating member to a mounting member.

Pivot assembly 100, FIG. 7A, is an alternative pivot assembly according to this invention. Rotating member 102 is pivotably interconnected with mounting member 104 by pivot pin 106. Pin 106 is received by opening 108 in rotating member 102 and threadably engages mounting member 104. Post 105 of mounting member 104 is engaged by an accessory clamp (not shown).

Rotating member 102 is held in a desired orientation by engagement of detent 110 and one of recesses 112 in mounting member 104. Engagement increase as rotating member 102 is tilted in the direction represented by arrow 113. Head 107 of pivot pin 106 inhibits translation of rotating member 102 along pivot axis 116.

When reorientation of rotating member 102 is desired, rotating member 102 is tilted about tilt axis 114 in the direction represented by arrow 115 to enable rotation about pivot axis 116. During tilting about tilt axis 114, end 118 of rotating member 102 is tilted into space 120 which is maintained between rotating member 102 and mounting member 104 by Bellville washer 122 which biases the members apart.

Figure 7B:
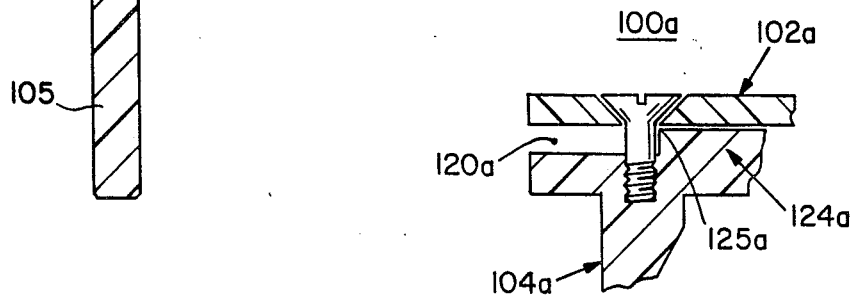
FIG. 7B is a partial cross-sectional view of another construction of the pivot assembly of FIG. 7A.

In another construction, space 124 between pivot pin 106 and detent 110 is instead occupied by solid structure, associated with one of rotating member 102 and mounting member 104, to establish space 120. Pivot assembly 100a, FIG. 7B, includes solid portion 124a of mounting member 104a. Rotating member 102a bears against point 125a and tilts into space 120a.

Figure 8A:
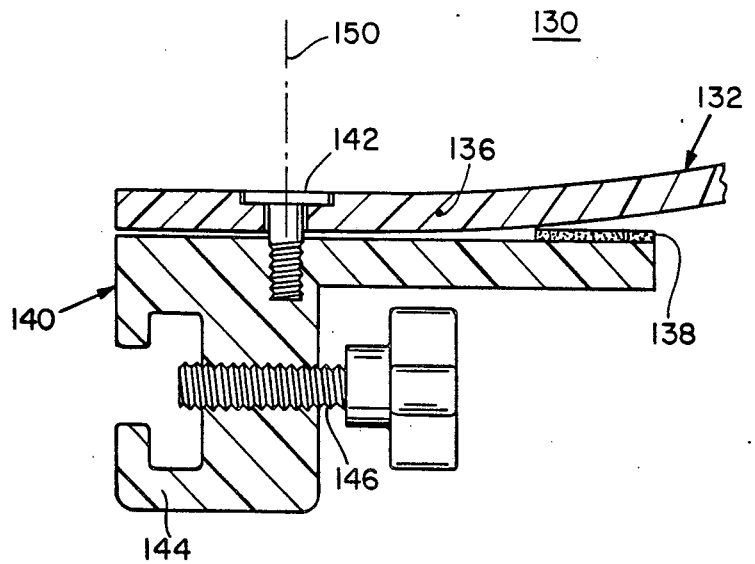
FIG. 8A is a schematic cross-sectional view of a still further pivot assembly according to this invention having a rotating member which flexes to accomplish tilting about a tilt axis to decrease gripping and enable rotation about a pivot axis.

Pivot assembly 130, FIG. 8A, represents yet another configuration in which rotating member 132 is formed of flexible material which enables bending of the distal end of rotating member 132 about tilt axis 136 and away from gripper 138. The flexible material enables flexing to decrease frictional engagement with gripper 138. The proximal end of rotating member 132 is pivotably interconnected to mounting member 140 by pivot pin 142. In this construction mount 140 includes clamp 144 which engages an accessory rail of an operating table and is secured to the accessory rail by screw 146. In other constructions mounting member 140 is the operating table itself which includes a hole to receive pivot pin 142.

Figure 8B:
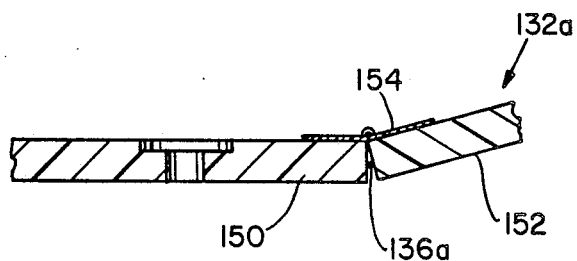
FIG. 8B is a partial cross-sectional view of a hinged rotating member.

In yet another construction, rotating member 132a, FIG. 8B, is formed of segments 150, 152 which are joined at tilt axis 136 by hinge element 154. Hinge element 154 may be a "living hinge", that is, a flexible piece of material, or may be a two-part hinge joined by a pin. In either case, hinge element 154 enables tilting of rotating member 132 about tilt axis 136a in a plane containing pivot axis 150. Further, in these constructions the tilt axis is both normal to and spaced from the pivot axis.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A pivot assembly comprising:
   a rotating member for supporting a load;
   a mounting member for supporting said rotating member;
   means for pivotably interconnecting said rotating member and said mounting member to enable rotation about a pivot axis, and for inhibiting translation of said rotating member relative to said mounting member along said pivot axis;
   means for enabling tilting of said rotating member about a tilt axis transverse to said pivot axis;
   said rotating member and said mounting member overlapping to define at least one pair of adjacent sections; and
   means for providing releasable gripping between said adjacent sections, responsive to the loading and tilting of said rotating member, to inhibit relative rotation about said pivot axis, by increasing grip between said adjacent sections when said rotating member supports a load and is torqued about said tilt axis in a first direction, and to permit relative rotation about said pivot axis by releasing grip when said rotating member is tilted about said tilt axis in a second and opposite direction, releasing said torque.

2. The pivot assembly of claim 1 in which said means for enabling includes means for defining a space between said rotating member and said mounting member, said rotating member tilting into said space during tilting about said tilt axis in said second direction.

3. The pivot assembly of claim 2 in which said means for defining includes spring means for biasing said rotating member and said mounting member away from each other.

4. The pivot assembly of claim 2 in which said means for defining is a portion of one of said members.

5. The pivot assembly of claim 1 in which said means for enabling includes hinge means associated with said rotating member.

6. The pivot assembly of claim 5 in which said rotating member is segmented and said hinge means includes structure hingeably joining the segments of said rotating member.

7. The pivot assembly of claim 1 in which said means for enabling includes flexible material forming at least a portion of said rotating member.

8. The pivot assembly of claim 1 in which said means for enabling establishes said tilt axis as spaced from said pivot axis.

9. The pivot assembly of claim 1 in which said means for enabling establishes said tilt axis as substantially normal to said pivot axis.

10. The pivot assembly of claim 1 in which said means for providing gripping includes a friction member mounted on at least one of said adjacent sections for providing frictional resistance to relative motion of said adjacent sections.

11. The pivot assembly of claim 10 in which said friction member is mounted on said rotating member.

12. The pivot assembly of claim 1 in which said means for providing gripping includes a detent on one of said adjacent sections and at least one recess on the other for receiving said detent.

13. The pivot assembly of claim 1 in which said mounting member includes a pair of spaced segments for receiving the proximate end of said rotating member therebetween.

14. The pivot assembly of claim 13 in which said rotating member and said mounting member define two pairs of adjacent sections and said means for providing gripping includes engaging means mounted on at least one section of each said pair of sections.

15. The pivot assembly of claim 1 in which said means for pivotably interconnecting includes a pivot pin.

16. The pivot assembly of claim 15 in which said pivot pin includes a head which inhibits translation of said rotating member.

17. The pivot assembly of claim 16 in which said pivot pin further includes means, spaced from said head, for engaging said mounting member.

18. The pivot assembly of claim 1 in which said rotating member, said mounting member, said means for pivotably interconnecting, said means for enabling rotation, and said means for providing gripping are radiologically translucent.

19. The pivot assembly of claim in which said rotating member, said mounting member, said means for pivotably interconnecting, said means for enabling rotation, and said means for providing gripping consist of non-magnetic and electrically non-conductive materials.

20. A pivot assembly for rotatably and lockably interconnecting an armboard and an armboard mount, comprising:
   means for pivotably interconnecting said armboard and said armboard mount to enable rotation about a pivot axis, and for inhibiting translation of said armboard away from said armboard mount along said pivot axis;

means for enabling tilting of said armboard about a tilt axis normal to said pivot axis;

said armboard and said armboard mount overlapping to define at least one pair of adjacent sections; and means for providing releasable gripping between said adjacent sections responsive to the loading and tilting of said armboard, to inhibit relative rotation about said pivot axis, by increasing grip between said adjacent sections when said armboard supports a load and is torqued about said tilt axis in a first direction, and to permit relative rotation about said pivot axis by releasing grip when said armboard is tilted about said tilt axis in a second and opposite direction, releasing said torque.

* * * * *